United States Patent [19]

Shu et al.

[11] 4,263,331
[45] Apr. 21, 1981

[54] FLAVORING WITH MIXTURE OF 2,5-DIMETHYL-3-ACETYL-FURAN AND 3,5-DI-(2-METHYLPROPYL)-1,2,4-TRITHIOLANE

[75] Inventors: Chi-Kuen Shu, Matawan; Braja D. Mookherjee, Holmdel; Manfred H. Vock, Locust, all of N.J.

[73] Assignee: International Flavors & Fragrances Inc., New York, N.Y.

[21] Appl. No.: 75,072

[22] Filed: Sep. 13, 1979

Related U.S. Application Data

[63] Continuation-in-part of Ser. No. 963,176, Nov. 24, 1978.

[51] Int. Cl.³ .............................................. A23L 1/226
[52] U.S. Cl. ..................................... 426/535; 426/536
[58] Field of Search ................................ 426/535, 536

[56] References Cited

U.S. PATENT DOCUMENTS 3,885,051 5/1975 Mussinan et al. ..................... 426/535

FOREIGN PATENT DOCUMENTS 623330 7/1961 Canada .

OTHER PUBLICATIONS

Furia et al., Fenaroli's Handbook of Flavor Ingredients, 2nd ed., 1975, vol. I, CRC Press: Cleveland pp. 134, 138, 143, 147, 149, 154, 176, 187, 188, 215.
Tjan et al., Synthesis of 3,5-Dialkyl-1,2,4, Trithianes, Tetrahedron, vol. 28, 1972, pp. 3489–3500.

*Primary Examiner*—Joseph M. Golian
*Attorney, Agent, or Firm*—Arthur L. Liberman

[57] ABSTRACT

Mixtures of 3,5-Di-(2-Methylpropyl)-1,2,4-Trithiolane having the formula:

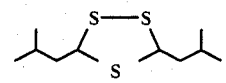

and its "cis" and "trans" isomers represented by the structures:

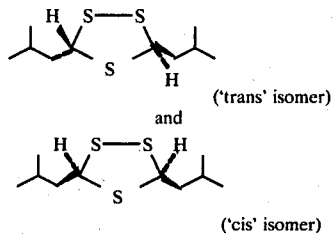

('trans' isomer)

and ('cis' isomer)

together with one or more 3-Acetyl-2,5-Dialkyl Furan or Thiophene compounds having the generic formula:

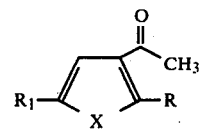

wherein X is sulfur or oxygen and R and $R_1$ is lower alkyl of 1 to 5 carbon atoms are described as being useful in augmenting or enhancing the organoleptic properties (taste and aroma) of foodstuffs.

1 Claim, 10 Drawing Figures

IR SPECTRUM, EXAMPLE I
"CIS" ISOMER.

NMR SPECTRUM, EXAMPLE I, FRACTION 5.

MASS SPECTRUM, EXAMPLE I, FRACTION 5.

IR SPECTRUM, EXAMPLE I, FRACTION 5

NMR SPECTRUM, EXAMPLE I, "TRANS" ISOMER

NMR SPECTRUM, EXAMPLE I, "CIS" ISOMER.

MASS SPECTRUM, EXAMPLE I, "TRANS" ISOMER.

IR SPECTRUM, EXAMPLE I, "TRANS" ISOMER.

MASS SPECTRUM, EXAMPLE I, "CIS" ISOMER

FLAVORING WITH MIXTURE OF 2,5-DIMETHYL-3-ACETYL-FURAN AND 3,5-DI-(2-METHYLPROPYL)-1,2,4-TRITHIOLANE

This application is a Continuation-in-Part of application for United States Letters Patent Ser. No. 963,176, filed on Nov. 24, 1978.

BACKGROUND OF THE INVENTION

The present invention relates to novel uses in foodstuffs and in foodstuff flavors of mixtures of 3,5-di(2-methylpropyl)-1,2,4-trithiolane or cis or trans isomers thereof having the structures:

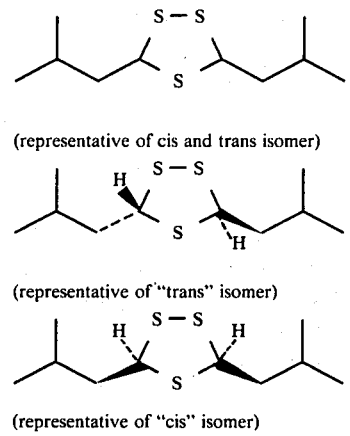

with 3-acetyl-2,5-dialkyl furans or thiophenes having the formula

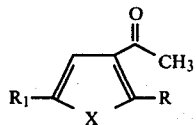

wherein X is sulfur or oxygen and R and $R_1$ are lower alkyl of 1 to 5 carbon atoms.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavor development in many foods is not understood. This is notable in products having roasted and smoked flavor characteristics, for example, roasted almond, roasted pork and smoked sesame flavor characteristics.

Reproduction of roasted, crisp bacon and pork rind flavors and aromas have been the subject of a long and continuing search by those engaged in the production of foodstuffs. The severe storage of foods, especially protein foods, in many parts of the world, have given rise to the need for utilizing non-meat sources of proteins and making such proteins as palatable and as meat-like as possible. Hence, materials which will closely simulate or exactly reproduce the flavor and aroma of roasted pork products are required.

Moreover, there are a great many meat containing or meat based foods presently distributed in a preserved form. Examples of these are condensed soups, dry-soup mixes, dry meat, freezedried or lyophilized meats, packaged gravies and the like. While the products contain meat or meat extracts, the fragrance, taste and other organoleptic factors are often impaired by the processing operation and it is desirable to supplement or enhance the flavors of these preserved foods with versatile materials which have either roasted pork or crisp bacon-like or pork rind-like or "roasted" aroma and taste nuances.

In U.S. Pat. No. 3,863,013, it is disclosed that five or six numbered heterocyclo compounds having two sulfur atoms in the ring are useful to alter the flavor or aroma of foodstuffs. The di-thioheterocyclic compounds disclosed as suitable according to U.S. Pat. No. 3,863,013 are represented by the following formulae:

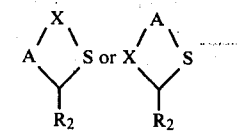

wherein X is

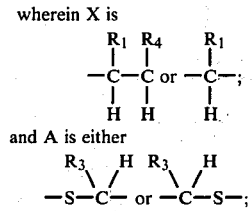

and A is either $$-S-\overset{R_3}{\underset{|}{C}}-\overset{H}{\underset{|}{C}}- \text{ or } -\overset{R_3}{\underset{|}{C}}-\overset{H}{\underset{|}{C}}-S-;$$

and each of $R_1$ to $R_4$ is hydrogen or a lower alkyl radical of one to three carbon atoms. Most of these compounds are disclosed at column 2 and 3 of U.S. Pat. No. 3,863,013 to have beef, garlic, vegetable and onion-type aromas and tastes, thusly:

"1,3-Dithiolane having the structure

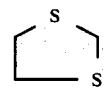

is described in Meadow, J. R. et al., J.A.C.S., Vol. 56, p. 2177 (1934) and U.S. Pat. No. 2,690,988. It has a sweet, sulfury character, which in high levels becomes reminiscent of degrading onions. It is useful for its sulfur notes in chocolate and coffee and roasted garlic notes found in stews, jellied veal dish and gravies. Taste threshold level is 2 parts per billion (2 ppb).

2-Methyl-1,3-dithiolane having the structure

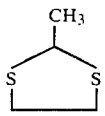

is described in J. Chem.Soc., B, (1970), p. 404 at p. 407 and U.S. Pat. No. 2,690,988. It has a cooked, roasted onion character. The background notes are suitable for stewed vegetable and vegetable protein hydrolyzate type flavors. Its taste threshold value is 20 ppb.

3,5-Dimethyl-1,2-dithiolane having the formula

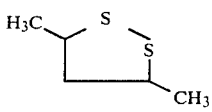

is described in Schotte, L., Arkiv. Kemi., Vol. 9, p. 441 (1956). It has a cooked onion note developing into a cooked vegetable nutty note. Its taste threshold value is 10 ppb.

3-Methyl-1,2-dithiolane having the formula

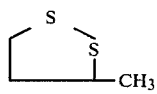

It has an oniony metallic taste with cooked beef or braised and vegetable nuances. It is suitable for stewed vegetable and braised beef flavors. Taste threshold level is 2 ppb.

2,4-Dimethyl-1,3-dithiolane having the structure

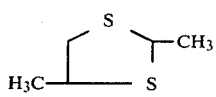

is described in Leggeter B. E. et al. in Can. J. Chem., Vol. 41, No. 10, p. 2671 (1963). It has an onion-like taste with slight metallic background notes and is suitable for stewed vegetable flavors. Its taste threshold value is 20 ppb.

4-Methyl-1,3-dithiolane having the structure

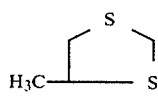

is generally described in U.S. Pat. No. 2,690,988. It has an oniony, root vegetable-like taste and is useful for stewed vegetable or braised beef type flavors. Its taste threshold value is 50 ppb.

1,2-Dithiane(ortho-dithiane) having the formula

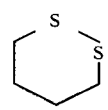

is described in Schoberl, A. Et al., Ann., Vol. 614, p. 66 (1958). It has a garlic character with slight metallic nuance and is suitable for stewed vegetable and horseradish flavors. Its taste threshold value is 2 ppb.

1,3-Dithiane(m-dithiane) having the formula

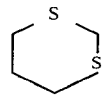

and has been described by Meadow & Read in J.A.C.S., Vol. 56, p. 2177 (1934). It has an onion, garlic-like taste with a metallic by-note and is suitable for meat alium flavors. Its taste threshold value is 50 ppb.

1,4-Dithiane) having the formula

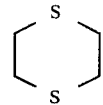

has been described in J. Chem. Soc., B, (1970), p. 404 at 407. It has an onion-like or garlic-like character and is useful for stewed vegetable type flavors. Its taste threshold value is 50 ppb.

2-Methyl-1,3-dithiane having the formula

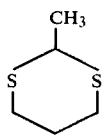

has been described by Autenreith, W. et al in Ber., 32, p. 1375 (1899). It has an onion-like character with metallic notes and is suitable for vegetable type flavors. Its taste threshold value is 20 ppb.

2,4-Dimethyl-1,3-dithiane having the formula

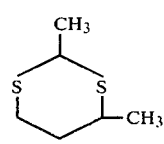

is described by Eliel et al., in J.A.C.S. Vol. 91, No. 10, p. 2703 (1969). It has an allium-onion like character with slight metallic notes and is suitable for onion flavors. Its taste threshold value is 5 ppb.

4-Methyl-1,3-dithiane having the formula

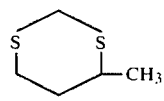

It has an onion, garlic and tomato like character and is suitable for stewed meats, gravy, tomato and onion flavors. It has a taste threshold level of 50 ppb.

2,4,6-Trimethyl-1,3-dithiane having the formula

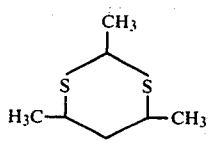

has been described by Eliel et al., J.A.C.S., 91, No. 10, p. 2703 (1969). It has a root vegetable-like character and is suitable for stewed vegetable or potato flavors. Its taste threshold is 10 ppb." Tetra and penta thiolane compounds are also disclosed for use in flavoring compositions for foodstuffs by U.S. Pat. Nos. 3,503,758 and 3,488,362. Thus, for example, in U.S. Pat. No. 3,503,758 compounds having the generic structure

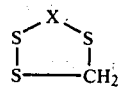

wherein X may be

—CH$_2$—S—,—CH$_2$—,

—CH$_2$—S—CH$_2$— or

—S—CH$_2$—S—

Specifically, the compounds: 1,2,3,5,6-pentathiepane (lenthionine); 1,2,3,5-tetrathiane; 1,2,4,6-tetrathiepane, and 1,2,4,5-tetrathiane indicated to be useful in, for example, enhancing pork and beef flavors.

A paper in Tetrahedron, Vol. 28, pages 3489-3500 (1972) entitled: "Synthesis of 3,5-Dialkyl-1,2,4-Trithiolanes/Assignment of Configuration and Conformational Analysis by PMR" by Tjan, Haakman, Teunis and Peer of the Unilever Research Duiven of the Netherlands discloses the synthesis of 3,5-dialkyl-1,2,4-trithiolanes of the structure:

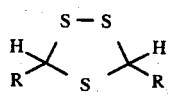

wherein R is disclosed to be either of methyl, ethyl, isopropyl or t-butyl. It is also disclosed by Tjan et al that such materials may be synthesized according to the technique of Asinger et al, Liebigs Ann. Chem. 627, 195 (1959).

Brinkman et al, J. Agr. Food Chem. 20,177 (1972) during their investigations into components contributing to beef flavor isolated from beef broth two volatile isomers which are tentatively identified as 3,5-dimethyl-1,2,4-trithiolanes. In addition, Chang et al Chem. Ind. (London) 1639 (1968) isolated two isomeric 3,5-dimethyl-1,2,4-trithiolanes from boiled beef and suggested that the isomers were in "cis" and "trans" forms but made no structural assignment. In paragraph 2 of the Tjan et al article, it was stated:

"... It was necessary to synthesize compound I (3,5-dimethyl-1,2,4-trithiolane, and in view of the promising properties; of the compounds as flavoring agents, we investigated a more general synthesis for 3,5-dialkyl-1,2,4-trithiolanes..."

Canadian Pat. No. 623,330 discloses and claims 1,2,4-trithiolanes having the formula:

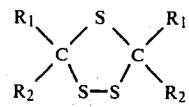

wherein $R_1$ is alkyl or hydrogen and $R_2$ is alkyl. Specifically disclosed are 3,5-di-n-propyl-1,2,4-trithiolane and 3,5-diethyl-1,2,4-trithiolane.

However, nothing in the prior art including subject matter mentioned in the Tjan et al article or in Canadian Pat. No. 623,330 suggests the synthesis and flavor use and flavor characteristics of the 3,5-di-(2-methylpropyl)-1,2,4-trithiolane or of its cis or trans isomers of our invention.

In addition, U.S. Pat. No. 3,885,051 issued on May 20, 1975 discloses 3-acetyl-2,5-dialkyl furan or thiophene compounds having the formula

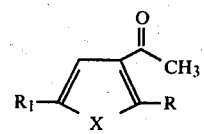

wherein X is sulfur or oxygen and R and $R_1$ is lower alkyl of 1 to 5 carbon atoms for augmenting or enhancing hazelnut, walnut and vanilla flavors.

However, nothing in the prior art suggests the synergistic effect of mixtures of 3-acetyl-2,5-dialkyl furans or thiophenes and 3,5-di-(2-methylpropyl)-1,2,4-trithiolanes particularly for use in augmenting or enhancing the flavor or aroma of a foodstuff.

THE INVENTION

Figure 1:
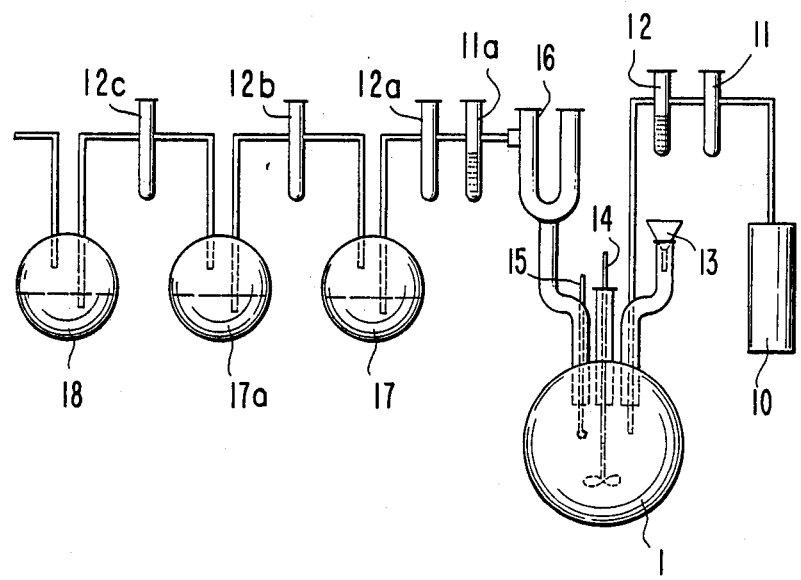
FIG. 1 is an illustration of the apparatus used in which the 3,5-di-(2-methylpropyl)-1,2,4-trithiolane of our invention is synthesized according to Example I.

The present invention provides mixtures of 3,5-di-(2-methylpropyl)-1,2,4-trithiolane and its cis and trans isomers having the structures:

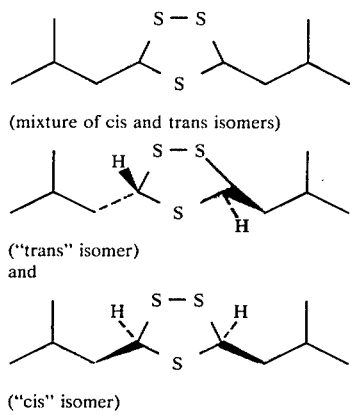

(mixture of cis and trans isomers)

("trans" isomer)
and ("cis" isomer)

and one or more 3-acetyl-2,5-dialkyl furan or thiophene compounds having the formula

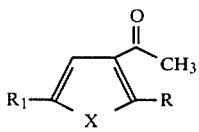

wherein X is sulfur or oxygen and R and $R_1$ is lower alkyl of 1 to 5 carbon atoms for augmenting or enhancing the organoleptic properties in foodstuffs, particularly hazelnut flavored foodstuffs. Such mixtures give rise to synergistic effects.

The synthesis of the 3,5-di-(2-methylpropyl)-1,2,4-trithiolane of our invention is carried out as taught by either Tjan et al, Tetrahedon, Vol. 28, pages 3489–3500 (1972) or according to Asinger et al, Liebigs Ann. Chem. 627,195 (1959) or according to the reaction scheme:

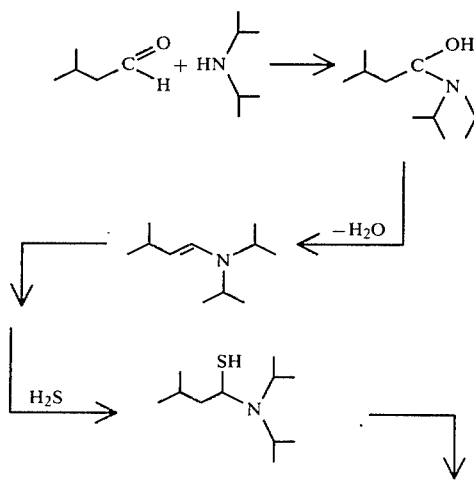

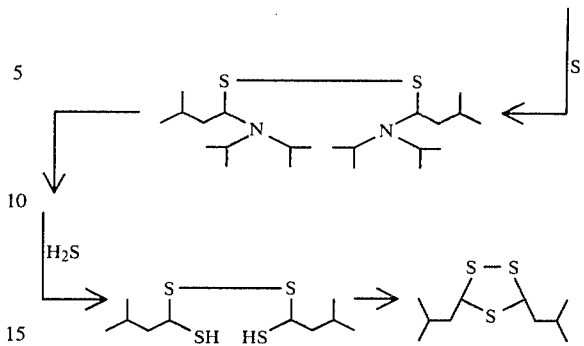

whereby isovaleraldehyde is first reacted with a dialkyl amine to form an enamine. The resulting enamine is reacted with hydrogen sulfide to form a mercaptan which is then oxidized to form a disulfide. The resulting disulfide is then again reacted with hydrogen sulfide to form a dimercaptan-disulfide which is then cyclized to form the 3,5-di-(2-methylpropyl)-1,2,4-trithiolane of our invention. The resulting 3,5-di-(2-methylpropyl)-1,2,4-trithiolane may be used as is for its organoleptic properties or the "cis" and "trans" isomers thereof may be separated by means of, for example, preparative column chromatography or preparative GLC.

The thus produced 3,5-di-(2-methylpropyl)-1,2,4-trithiolane and cis and trans isomers thereof of our invention have roasted, roasted nut, crisp bacon-like and pork rind-like aroma and flavor characteristics making the 3,5-di-(2-methylpropyl)-1,2,4-trithiolane suitable for use in flavors which can be described as "roasted almond flavors", "roasted hazelnut flavors", "roasted peanut flavors", "roasted pork" flavors, coffee flavors, caramel flavors and "roasted sesame seed" flavors. Thus, the 3,5-di-(2-methylpropyl)-1,2,4-trithiolane and its cis and trans isomer of our invention can be used to alter, vary, fortify, modify, augment, enhance or otherwise improve their organoleptic properties including flavor and/or aroma of a wide variety of materials which are ingested, consumed or otherwise organoleptically sensed.

The 3-acetyl-2,5-dialkyl furans or thiophenes can be prepared according to Example I or II at columns 6 and 7 of the U.S. Pat. No. 3,885,051 issued on May 20, 1975.

The mixtures of 3-acetyl-2,5-dialkyl furan or thiophene compounds and 3,5-di-(2-methylpropyl)-1,2,4-trithiolanes of our invention may be prepared by intimately admixing the 3-acetyl-2,5-dialkyl furan or thiophene compounds and 3,5-di-(2-methylpropyl)-1,2,4-trithiolanes in a blender in proportions of from 0.1 part 3-acetyl-2,5-dialkyl furan or thiophene: 0.9 parts 3,5-di-(2-methylpropyl)-1,2,4-trithiolane up to 0.9 parts 3-acetyl-2,5-dialkyl furan or thiophene: 0.1 part 3,5-di-(2-methylpropyl)-1,2,4-trithiolane.

The terms "alter and modify" in their various forms will be understood herein to mean the supplying or imparting a flavor character or note to an otherwise bland relatively tasteless substance, or augmenting an existing flavor characteristic where the natural flavor is deficient in some regard, or supplementing the existing flavor or aroma impression to modify the organoleptic character. The materials which are so altered or modified are generally referred to herein as consumable materials.

The term "enhance" as used herein is intended to mean the intensification of a flavor or aroma characteristic, note or nuance without the modification of the quality thereof. Thus "enhancement" of a flavor or aroma means that the enhancement agent does not add any additional flavor note or nuance in the concentration utilized (based upon the weight of foodstuff in which it is utilized).

The mixtures of 3-acetyl-2,5-dialkyl furans or thiophenes and 3,5-di-(2-methylpropyl)-1,2,4-trithiolanes of this invention are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma to a consumable article.

The term "foodstuff" as used herein includes both solid and liquid ingestible materials for man or animals, which materials usually do, but need not, have nutritional value. Thus, foodstuffs includes meats, gravies, soups and convenience food, vegetables, snack foods, dog and cat foods, other veterinary products, and the like.

When the mixtures of 3,5-di-(2-methylpropyl)-1,2,4-trithiolane or its "cis" or "trans" isomers taken together with 3-acetyl-2,5-dialkyl furans or thiophenes according to this invention are used in a food flavoring composition, they can be combined with conventional flavoring materials or adjuvants. Such co-ingredients or flavoring adjuvants are well known in the art for such use and have been extensively described in the literature. SUch adjuvant material is required (1) to be substantially non-reactive with the mixtures of 3,5-di-(2-methylpropyl)-1,2,4-trithiolane or its "cis" or "trans" isomers taken together with 3-acetyl-2,5-dialkyl furans or thiophenes used in our invention particularly whereby unwanted detrimental organoleptic properties are not created in the overall organoleptic impression of the ultimate foodstuff used; (2) to be, taken alone or taken together with other materials used in conjunction therewith, ingestibly acceptable from an aesthetic standpoint and from an organoleptic standpoint; (3) to be non-toxic and (4) to be otherwise non-deleterious. Apart from these requirements, conventional materials can be used and broadly include other flavor materials, vehicles, stabilizers, thickeners, surface active agents, conditioners, and flavor intensifiers.

Examples of preferred co-flavoring adjuvants are:
Methyl thiazole alcohol (4-methyl-5-beta-hydroxyethyl thiazole);
2-Methyl butanetiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
2-Methylfuran-3-thiol;
2-Methyldihydrofuran-3-thiol;
2-Methyltetrahydrofuran-3-thiol;
2-Ethylfuran-3-thiol;
2-Ethyldihydrofuran-3-thiol;
2-Ethyltetrahydrofuran-3-thiol;
2-Propylfuran-3-thiol;
2-Isopropylfuran-3-thiol;
2-Isopropyldihydrofuran-3-thiol;
2-Isopropyltetrahydrofuran-3-thiol;
2-Propyldihydrofuran-3-thiol;
2,5-Dimethylfuran-3-thiol;
2,5-Dimethyldihydrofuran-3-thiol;
2,5-Dimethyltetrahydrofuran-3-thiol;
2,5-Diethylfuran-3-thiol;
2,5-Diethyldihydrofuran-3-thiol;
2,5-Diethyltetrahydrofuran-3-thiol;
2-Ethyl-5-methylfuran-3-thiol;
2-Methyl-5-ethylfuran-3-thiol;
2-Ethyl-5-methyldihydrofuran-3-thiol;
2-Ethyl-5-methyltetrahydrofuran-3-thiol;
2,5-Dipropylfuran-3-thiol;
2,5-Diisopropylfuran-3-thiol;
5-Isopropyl-2-methylfuran-3-thiol;
2-Butylfuran-3-thiol;
2-Ethyl-5-propyltetrahydrofuran-3-thiol;
Bis(2-methyl-3-furyl)sulfide;
Bis(2-methyl-3-furyl)disulfide;
Bis(2-ethyl-3-furyl)sulfide;
Bis(2-ethyl-3-furyl)disulfide;
Bis(2,5-dimethyl-3-furyl)sulfide;
Bis(2,5-dimethyl-3-furyl)disulfide;
Bis(2-methyl-3-dihydrofuryl)sulfide;
Bis(2-methyl-3-tetrahydrofuryl)sulfide;
Bis(2-methyl-3-tetrahydrofuryl)disulfide;
Bis(2-methyl-3-dihydrofuryl)disulfide;
Bis(2,5-diethyl-3-furyl)sulfide;
Bis(2-ethyl-5-methyl-3-furyl)disulfide;
Bis(2,5-diethyl-3-furyl)disulfide;
Bis(2,5-dipropyl-3-furyl)disulfide;
Bis(2,5-dipropyl-3-furyl)sulfide;
Bis(2,5-dibutyl-3-furyl)disulfide;
Bis(5-ethyl-2-methyl-3-dihydrofuryl)disulfide
Bis(2-isopropyl-3-furyl)sulfide;
Bis(2-isopropyl-3-furyl)disulfide;
Bis(2-isopropyl-3-dihydrofuryl)sulfide;
Bis(2-isopropyl-3-tetrahydrofuryl)disulfide;
Alkyl pyrazine;
Methyl pyrazine;
2-Ethyl-3-methyl pyrazine;
Tetramethyl pyrazine;
Dipropyl disulfide;
Methyl venzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenol acetaldehyde;
ω-Decalactone;
ω-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Cysteine;

Hydrolyzed vegetable protein;
Hydrolyzed fish protein;
Tetramethyl pyrazine;
3-acetyl-2,5-dimethylfuran; and
3-acetyl-2,5-dimethylthiophene.

The mixtures of 3,5-di-(2-methylpropyl)-1,2,4-trithiolane or its "cis" or "trans" isomers taken together with 3-acetyl-2,5-dialkyl furans or thiophenes or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The mixtures of 3,5-di-(2-methylpropyl)-1,2,4-trithiolane or its "cis" or "trans" isomers taken together with 3-acetyl-2,5-dialkyl furans or thiophenes according to this invention can be incorporated with the carriers by conventional means such as spray-drying, drum-drying, and the like. Such carriers can also include materials for coacervating the mixtures of 3,5-di-(2-methylpropyl)-1,2,4-trithiolane or its "cis" or "trans" isomers taken together with 3-acetyl-2,5-dialkyl furans or thiophenes (and other flavoring ingredients, as present) to provide encapsulated products. When the carrier is an emulsion the flavoring composition can also contain emulsifiers such as mono- and diglycerides of fatty acids and the like. With these carriers or vehicles, the desired physical form of the composition can be prepared.

The quantity of the mixtures of 3,5-di-(2-methylpropyl)-1,2,4-trithiolane or its "cis" or "trans" isomers taken together with 3-acetyl-2,5-dialkyl furans or thiophenes should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate compositions contain from about 0.0005 parts per million (ppm) to about 250 ppm of mixtures of 3,5-di-(2-methylpropyl)-1,2,4-trithiolane or its "cis" or "trans" isomers taken together with 3-acetyl-2,5-dialkyl furans or thiophenes. More particularly, in food compositions, it is desirable to use from about 0.005 ppm to 100 ppm to enhancing flavors and in certain preferred embodiments of the invention, from about 0.2 to 50 ppm of the derivatives are included to add positive flavors to the finished product. All parts, proportions, percentages, and ratios herein are by weight unless otherwise indicated.

The amount of the mixtures of 3,5-di-(2-methylpropyl)-1,2,4-trithiolane or its "cis" or "trans" isomers taken together with 3-acetyl-2,5-dialkyl furans or thiophenes of our invention to be utilized in flavoring compositions can be varied over a wide range to the foodstuff. Thus, amounts of one or more derivatives according to the present invention of from about 2 ppm up to 80 or 90 percent of the total flavoring composition can be incorporated in such compositions. It is generally found to be desirable to include from about 10 ppm up to about 20 percent of the mixture of 3,5-di-(2-methylpropyl)-1,2,4-trithiolane or its "cis" or "trans" isomers taken together with 3-acetyl-2,5-dialkyl furans or thiophenes in such compositions.

The following examples are given to illustrate embodiments of the invention as it is preferably preferred to practice it. It will be understood that these examples are illustrative and the invention is not to be considered as restricted thereto except as indicated in the appended claims.

EXAMPLE I

PREPARATION OF 3,5-DI-(2-METHYLPROPYL)-1,2,4-TRITHIOLANE AND ITS CIS AND TRANS ISOMERS

Reaction:

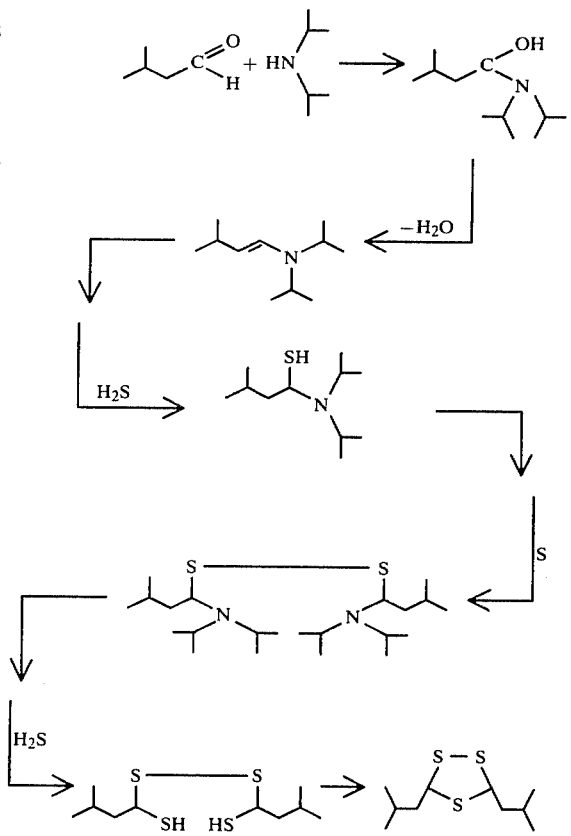

Using the apparatus illustrated in FIG. 1, into a 1 liter 3-necked flask (1, fitted with a thermometer (15) stirrer (14) and addition funnel (13) and an isopropyl alcohol/dry-ice condenser (16) is placed diisopropyl enamine (1 mole, 1ol grams) over a period of 20 minutes, dropwise. The diisopropyl amine is cooled by means of an ice/salt mixture at 5° C. with stirring. The diisopropyl amine is stirred for a period of 30 minutes. Isovaleric aldehyde (1 mole, 86 grams) is added dropwise from the dropping funnel (13) at such a rate that the temperature remains at 0°-5° C. The addition of the isovaleraldehyde takes place over a period of 30 minutes. The mixture is then stirred vigorously for about 2 hours. Hydrogen sulfide is then doubled in to the reaction flask (1) from cylinder (10) until saturation. Any hydrogen sulfide which evolves unreacted from reaction flask (1) is trapped in the Primol ® trap (Primol ® is a registered trademark of the Exxon Corporation of Linden, New Jersey for identifying a hydrocarbon edible mineral oil), and (11a); and empty traps (12, 12a, 12b and 12c); and 40% sodium hydroxide aqueous liquid containing traps (17 and 17a) and a chlorox trap (containing a solution of sodium hypochloride) (18).

Sulfur (0.5 moles, 16 grams) is then added to the reaction mass in small portions while stirring for a period of one hour and maintaining the reaction temperature at 0°–5° C. The resulting mixture is then allowed to come to room temperature and stirred for a period of four hours. The resulting organic oil is acidified with 2 molar acetic acid and then extracted with diethyl ether. The ether extract is washed with water and dried over anhydrous magnesium sulfate. The dried ether extract is then evaporated on a rotary evaporator yielding a crude material weighing 106 grams. 60% of this crude material is the product 3,5-di-(2-methylpropyl)-1,2,4-trithiolane having the structure:

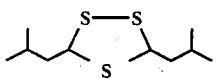

Accordingly, the yield equals 36%. The crude material is distilled on a micro distillation column after adding thereto 10 grams of Primol ® yielding the following fractions:

| No. | Vapor Temp. | Liquid Temp. | Vac. mmHg | Wt. g. | purity % |
|---|---|---|---|---|---|
| 1 | 64–100 | 114–124 | 0.45 | | |
| 2 | 102 | 127 | 0.45 | | |
| 3 | 102 | 129 | 0.45 | 3.0 | 96.2% |
| 4 | 102 | 133 | 0.45 | 6.6 | 98.0 |
| 5 | 102 | 137 | 0.45 | 3.8 | 98.0 |
| 6 | 106 | 148 | 0.45 | 6.7 | 94.5 |
| 7 | 113 | 171 | 0.45 | 83 | |
| 8 | 120 | 175 | 0.45 | 11.2 | |
| 9 | 130 | 184 | 0.45 | 19.0 | |

The fraction 5 of the distillate then separated into two isomers using a Carbowax 20 M GLC column, a cis isomer and a trans isomer.

Figure 2:
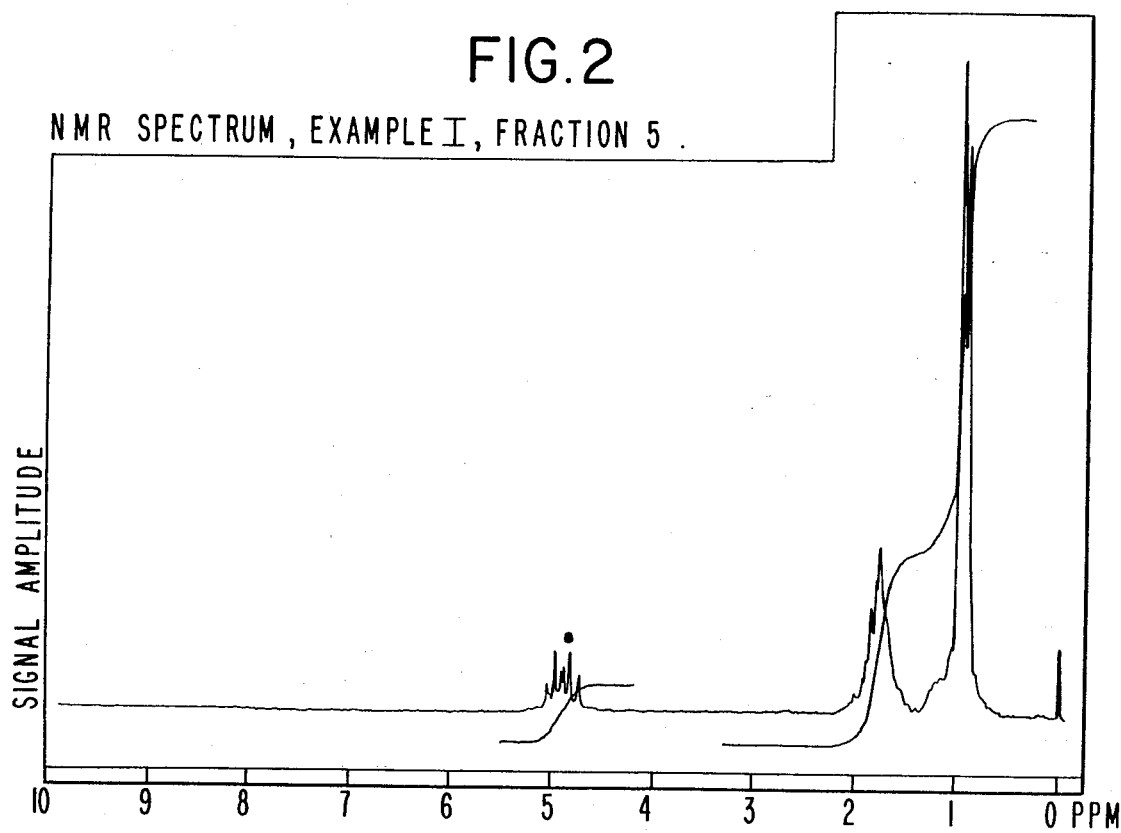
FIG. 2 is the NMR spectrum for fraction 5 of the 3,5-di-(2-methylpropyl)-1,2,4-trithiolane of our invention (mixture of cis and trans isomers) produced according to Example I.
Figure 3:
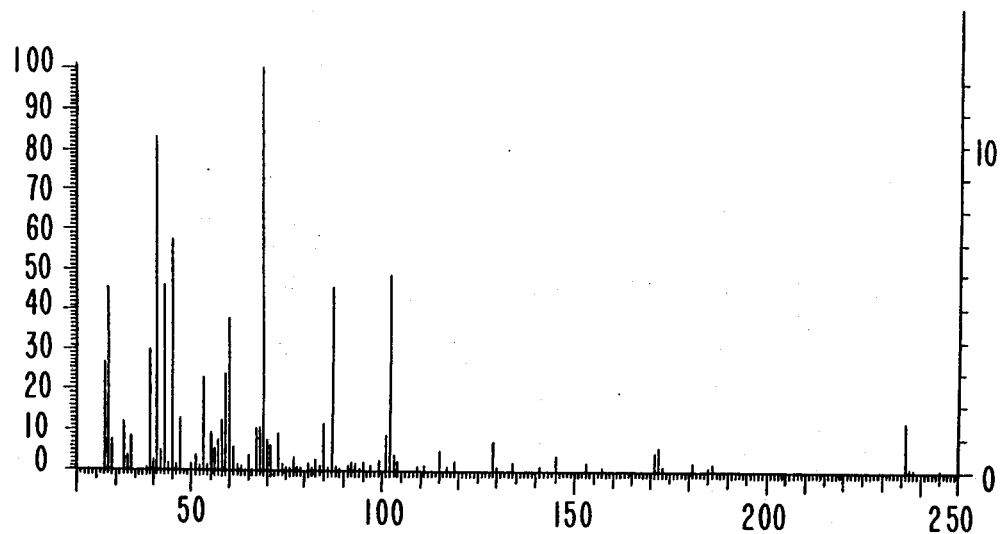
FIG. 3 is the mass spectrum for fraction 5 of the mixture of cis and trans isomers of 3,5-di-(2-methylpropyl)-1,2,4-trithiolane produced according to Example I.
Figure 4:
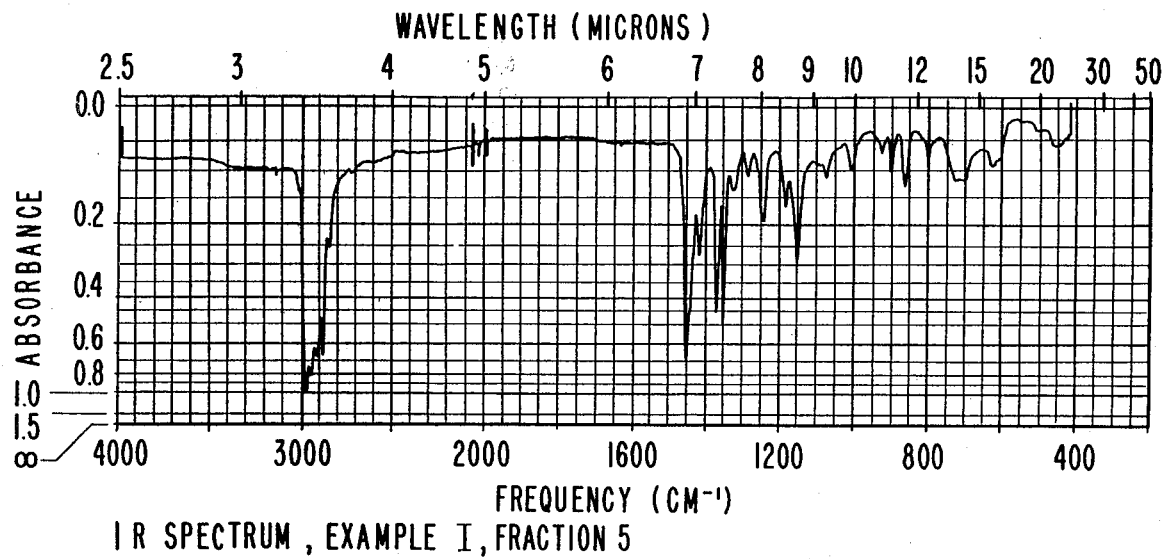
FIG. 4 is the infrared spectrum for the mixture of cis and trans isomers of 3,5-di-(2-methylpropyl)-1,2,4-trithiolane of fraction 5 produced according to Example I.

FIG. 2 is the NMR spectrum for fraction 5. FIG. 3 is the mass spectrum for fraction 5. FIG. 4 is the infrared spectrum for fraction 5. Fraction 5 contains a mixture of "cis" and "trans" isomers of 3,5-di-(2-methylpropyl)-1,2,4-trithiolane having the structure:

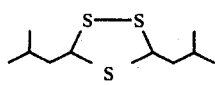

Figure 5:
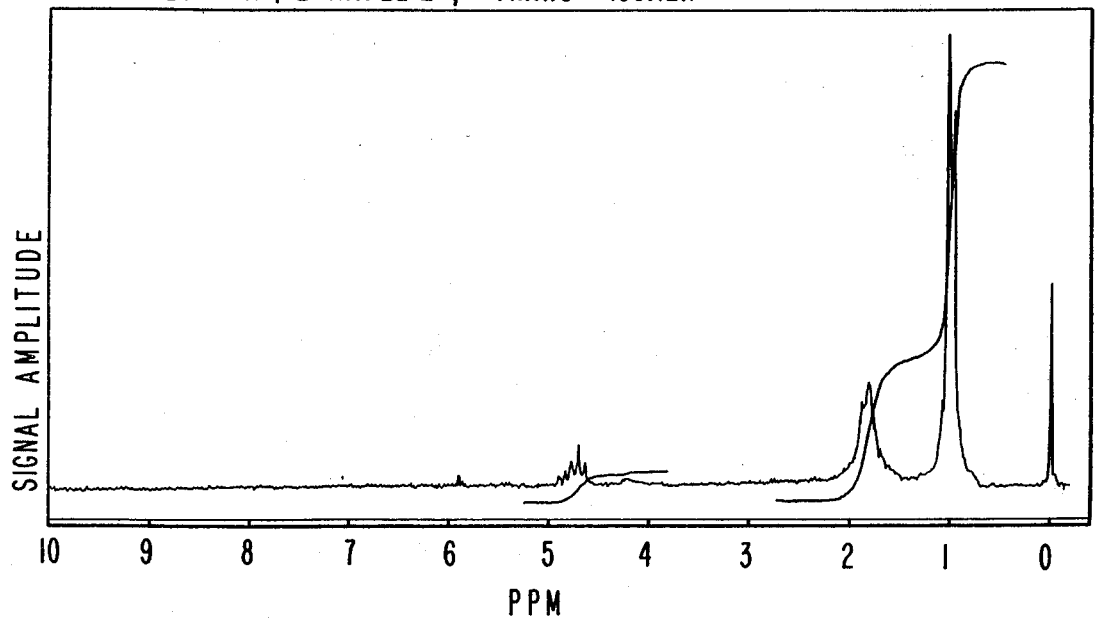
FIG. 5 is the NMR spectrum for the trans isomer of 3,5-di-(2-methylpropyl)-1,2,4-trithiolane produced according to Example I.

FIG. 5 is the NMR spectrum for the "trans" isomer of 3,5-di-(2-methylpropyl)-1,2,4-trithiolane having the structure:

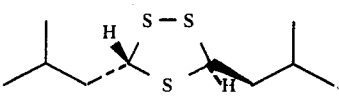

Figure 6:
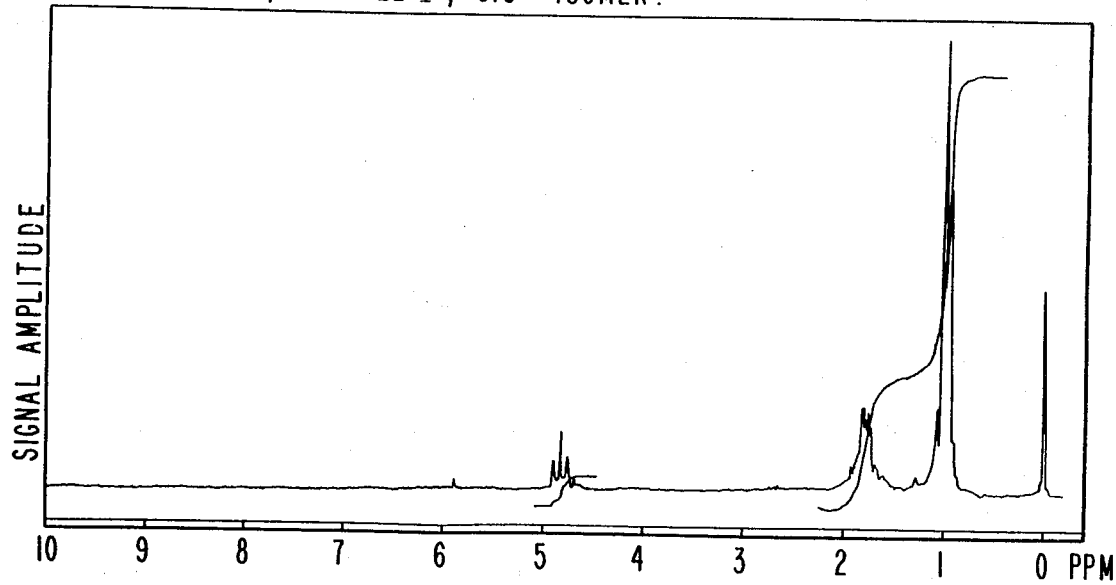
FIG. 6 is the NMR spectrum for the cis isomer of 3,5-di-(2-methylpropyl)-1,2,4-trithiolane produced according to Example I.

FIG. 6 is the NMR spectrum for the "cis" isomer of 3,5-di-(2-methylpropyl)-1,2,4-trithiolane having the structure:

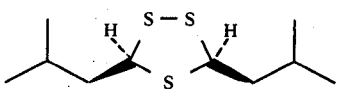

Figure 7:
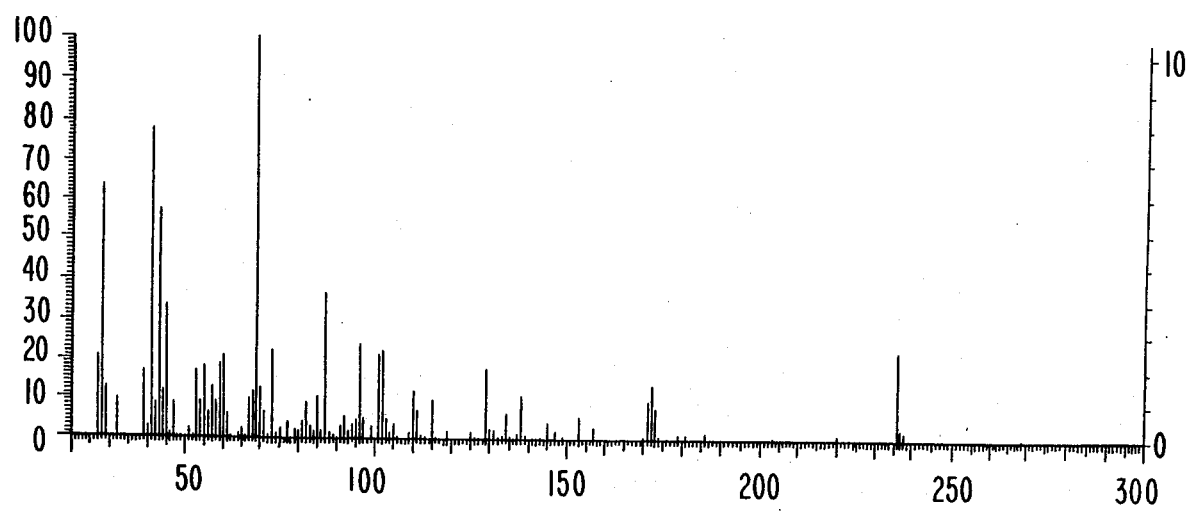
FIG. 7 is the mass spectrum for the trans isomer of 3,5-di-(2-methylpropyl)-1,2,4-trithiolane produced according to Example I.

FIG. 7 is the mass spectrum for the "trans" isomer of 3,5-di-(2-methylpropyl)-1,2,4-trithiolane.

Figure 8:
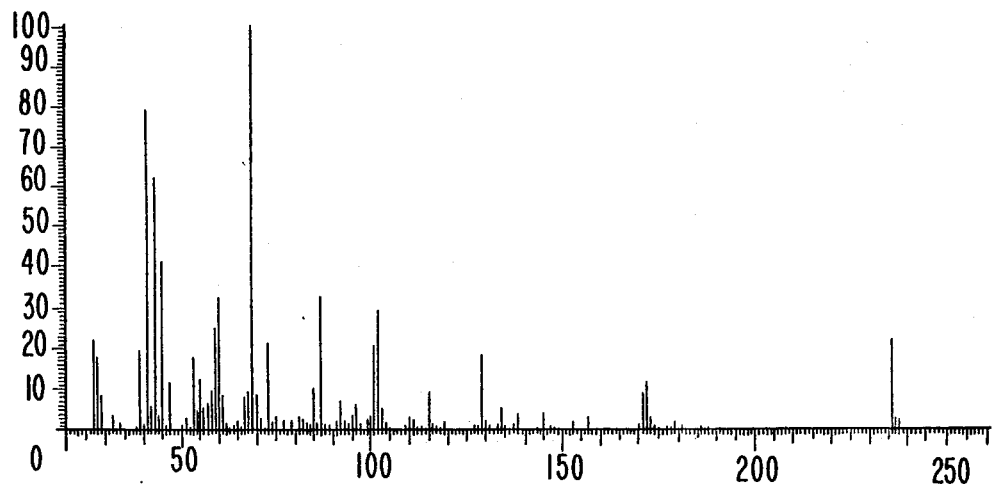
FIG. 8 is the mass spectrum for the cis isomer of 3,5-di-(2-methylpropyl)-1,2,4-trithiolane produced according to Example I.

FIG. 8 is the mass spectrum for the "cis" isomer of 3,5-di-(2-methylpropyl)-1,2,4-trithiolane.

Figure 9:
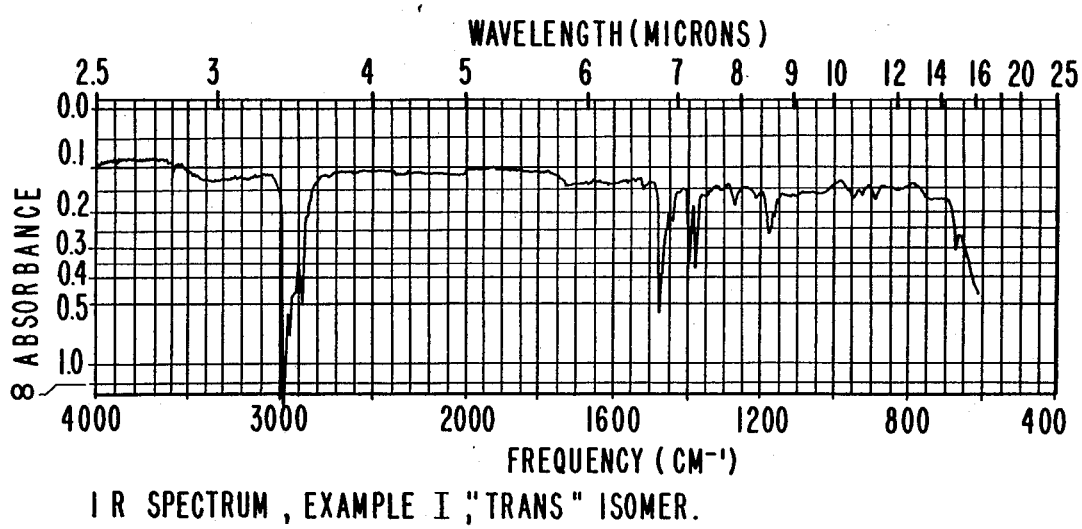
FIG. 9 is the infrared spectrum for the trans isomer of 3,5-di-(2-methylpropyl)-1,2,4-trithiolane produced according to Example I.

FIG. 9 is the infrared spectrum for the "trans" isomer of 3,5-di-(2-methylpropyl)-1,2,4-trithiolane.

Figure 10:
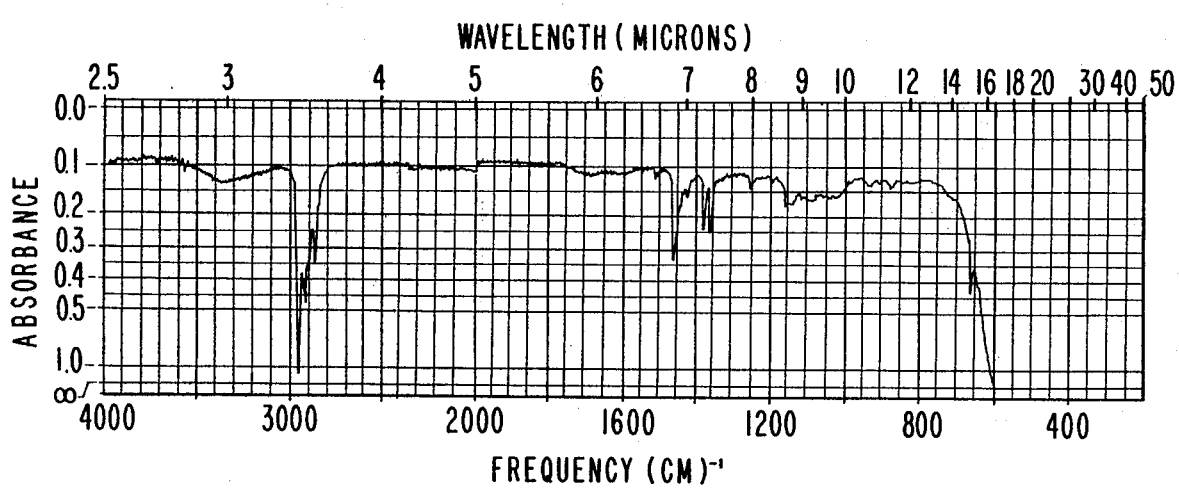
FIG. 10 is the infrared spectrum for the "cis" isomer of 3,5-di-(2-methylpropyl)-1,2,4-trithiolane produced according to Example I.

FIG. 10 is the infrared spectrum for the "cis" isomer of 3,5-di(2-methylpropyl)-1,2,4-trithiolane.

Fraction 5 is indicated at 1 ppm to have a roasted, crisp bacon-like, pork rind-like aroma and flavor characteristic.

EXAMPLE II

The following ingredients are refluxed for four hours:

| Ingredient | Parts by Weight |
|---|---|
| L-Cysteine hydrochloride | 0.9 |
| Carbohydrate-free vegetable protein hydrolysate | 30.9 |
| Thiamine hydrochloride | 0.9 |
| Water | 67.30 |

The resulting mixture is then aged for 3 days and an aliquot portion is withdrawn and dried. Based on the weight of the dry solid obtained, sufficient gum arabic is added to the batch to provide a composition containing one part by weight of gum arabic. The composition is then spray-dried.

A mixture if "cis" and "trans" isomers of 3,5-di(2-methylpropyl)-1,2,4-trithiolane (fraction 5) produced according to Example I is added to the spray-dried material to a concentration of 3 ppm. The resulting material has an excellent roast pork flavor.

EXAMPLE III

A roast pork flavored gravy is made by formulating a composition in the amounts indicated under ingredient and parts by weight:

| Ingredient | Parts by Weight |
|---|---|
| Cornstarch | 10.50 |
| The final product produced according to Example II | 3.00 |
| Caramel color | .30 |
| Garlic powder | .05 |
| White pepper | .05 |
| Salt | 1.92 |
| Monosodium glutamate | .20 |

To one unit of gravy flavor concentrate, eight ounces of water is added, and the mixture is stirred thoroughly to disperse the ingredients, brought to a boil, simmered for 1 minute and served. This "meatless" pork flavored gravy exhibits an excellent unique sweet roasted pork flavor.

EXAMPLE IV 3,5-di-(2-methylpropyl)-1,2,4-trithiolane (fraction 5 produced according to Example I) is added to beef broth (Wyler's beef broth) prepared from a commercial dried mixture and 250 ml hot water to yield a final concentration of 2 ppm of 3,5-di-(2-methylpropyl)-1,2,4-trithiolane. The 3,5-di-(2-methylpropyl)-1,2,4-trithiolane increases the sweet meat, smoked and pork rind-like character and enhances the broth-like note. The resultant beef broth has an improved more blended sweet meaty flavor and pork-type flavor than does the unflavored beef broth.

EXAMPLE V

The following ground sausage mixture is prepared:

| Ingredient | Parts by Weight |
|---|---|
| Ground Beef | 200 |
| Beef suet | 120 |
| Ice/NaCl (50:50 mixture) | 200 |
| Potato flour | 100 |
| Anhydrous bread crumbs | 140 |
| Dry milk powder | 20 |
| Standard spice flour* | 10 |

*The standard spice flavor contains:

| Ingredient | Parts by Weight |
|---|---|
| Oil of cumin | 1.5 |
| Oil of mustard | 3.5 |
| Oil of celery | 3.5 |
| Oil of ginger | 5.0 |
| Oil of cloves | 14.5 |
| Oil of coriander | 18.0 |
| Oil of pimenta berries | 22.0 |
| Oil of black pepper | 45.0 |
| Oleoresin capsicum | 375.0 |
| Oil of nutmeg | 500.0 |

To the above mixture 0.02% by weight of the following mixture is added:

| Ingredient | Parts by Weight |
|---|---|
| 3,5-di(2-methylpropyl)-1,2,4-trithiolane (prepared according to Example I, fraction 5) | 5 |
| Ethyl alcohol | 95 |

The resulting mixture is then formed into a sausage and encased in the usual manner. The encased sausage is heated in water at a temperature of 160°–180° F. for a period of 2 hours. This sausage has a sweet pork-taste with crisp bacon nuances reminiscent of the taste of sausage made with natural pork.

EXAMPLE VI

The following mixture is prepared:

| Ingredient | Formula A Parts by Weight |
|---|---|
| ethyl maltol | 1 |
| maltol | 2 |
| vanillin | 4 |
| methyl cyclopentenolone | 5 |
| benzaldehyde | 1 |
| resorcin dimethyl ether 0.1% (in 95% ethyl alcohol) | 1 |
| absolute Fenugreek 1% (in 95% ethyl alcohol) | 5 |
| ethyl oleate | 1 |
| gamma-nonalactone 1% (in 95% ethyl alcohol) | 5 |
| trimethyl pyrazine 0.1% (in 95% ethyl alcohol) | 2 |
| 2-ethyl-5-methyl pyrazine 0.1% (in 95% ethyl alcohol) | 1 |
| alcohol 95% | 12 |
| propylene glycol | 60 |

To Formulation A, 0.1 part of 3,5-di-(2-methylpropyl)-1,2,4-trithiolane (prepared according to Example I, fraction 5) is added and the resulting mixture is evaluated by a bench panel of four members. The conclusion of the bench panel is that the 3,5-di-(2-methylpropyl)-1,2,4-trithiolane contributes a roasted nuance to this hazelnut-like formulation and causes it to be more natural-like.

To Formula A with 0.01 part of 3,5-di-(2-methylpropyl)-1,2,4-trithiolane, 0.1 part of 3-acetyl-2,5-dimethylfuran is also added and resulting mixture is evaluated by a bench panel of four members. The conclusion of the bench panel is that the mixture of 3-acetyl-2,5-dimethylfuran and 3,5-di-(2-methylpropyl)-1,2,4-trithiolane (in a 5:50 ratio, weight:weight) gives rise to an interesting roasted hazelnut flavor with sweet, dried nuances. It is the opinion of the bench panel in addition that the combination of 3-acetyl-2,5-dimethylfuran and 3,5-di-(2-methylropyl)1,2,4-trithiolane is a synergistic combination giving rise to organoleptic properties over and above the sum total of the two individual compounds.

EXAMPLE VII

The following mixture is prepared:

| Ingredients | Parts by Weight |
|---|---|
| Ethyl Maltol | 1 |
| Maltol | 2 |
| Vanillin | 4 |
| Methyl Cyclopentenolone | 5 |
| Benzaldehyde | 1 |
| Resorcin Dimethyl Ether 0.1% (in 95% ethyl alcohol) | 1 |
| Absolute Fenugreek 1% (in 95% ethyl alcohol) | 5 |
| Ethyl Oleate | 1 |
| Gamma-Nonalactone 1% (in 95% ethyl alcohol) | 5 |
| Trimethyl Pyrazine 0.1% (in 95% ethyl alcohol) | 2 |
| 2-Ethyl-5-Methyl Pyrazine 0.1% (in 95% ethyl alcohol) | 1 |
| Alcohol 95% | 12 |
| Propylene Glycol | 60 |

The formulation is admixed with the material to be tested and the resulting admixture is diluted in water at the rate of 100 ppm. The water solutions are compared at equal intensity levels. Each of the test solutions is tasted and smelled. This is a subjective test but an accepted procedure for evaluating the relative suitability of candidate compounds and mixtures as ingredients in foodstuffs if the test is carried out by a professional flavorist or flavor chemist.

The investigations described above comparing the taste and aroma of solutions of equal intensity of test compounds and mixture give rise to the following results:

A. The Basic Flavor Formulation supra is compared with and without the addition of 0.1% 3,5-di-(2-methylpropyl)-1,2,4-trithiolane at the rate of 100 ppm in water. The flavor with the 3,5-di-(2-methylpropyl)-1,2,4-trithiolane has additional roasted, roasted hazelnut notes missing in the flavor without the 3,5-di-(2-methylpropyl)-1,2,4-trithiolane. Therefore, the flavor with the 3,5-di-(2-methylpropyl)-1,2,4-trithiolane is preferred by all panel members when tested by a bench panel.

B. The Basic Formulation, supra, is compared with and without the addition of 0.1% 2,5-dimethyl-3-acetylfuran at the rate of 100 ppm in water. The flavor with the 2,5-dimethyl-3-acetylfuran has sweet, dried/light roasted hazelnut and notes as found in haxelnut paste. Therefore, the flavor with the 2,5-dimethyl-3-acetylfuran has been preferred by all panel members when tested by a bench panel of five members.

C. The Basic Formulation, supra, is compared with the addition of 0.1% 3,5-di-(2-methylpropyl)-1,2,4-trithiolane and 0.1% of 3-acetyl-2,5-dimethylfuran against the flavor formulations as in "A" and "B" at 100 ppm in water. The taste is over-roasted and nearly bacon-roasted like. Therefore, the bench panel concluded that there is a synergistic effect resulting from the use of 3,5-di-(2-methylpropyl)-1,2,4-trithiolane.

D. The Basic Formulation, supra, has been compared with the addition of 0.01% 3,5-di-(2-methylpropyl)-1,2,4-trithiolane and 0.1% of 2,5-dimethyl-3-acetylfuran at the rate of 100 rpm. The taste of this combination is better than the flavors of "A, B, or C"; pleasant, roasted hazelnut character with good dried, sweet, hazelnut notes. It is obvious that the material, 3,5-di-(2-methylpropyl)-1,2,4-trithiolane has, together with the compound 2,5-dimethyl-3-acetylfuran, a synergistic effect on the roasted notes. All panel members preferred the combination of "D" over all other combinations or the basic formulations.

The foregoing results give rise to the conclusion that the combination either in a 1:1 ratio or in 1:0.1 ratio of 2,5-dimethyl-3-acetylfuran:3,5-di-(2-methylpropyl)-1,2,4-trithiolane has organoleptic effects insofar as augmenting or enhancing foodstuff flavors which effect is considered to be "synergistic" when compared to the organoleptic properties of the individual materials of the mixture:

(i) 3,5-di-(2-methylpropyl)-1,2,4-trithiolane; and (ii) 2,5-dimethyl-3-acetylfuran and this organoleptic effect which is synergistic is unexpected, unobvious and advantageous given the properties of the individual compounds of the combination, namely, 2,5-dimethyl-3-acetylfuran and 3,5-di-(2-methylpropyl)-1,2,4-trithiolane.

What is claimed is:

1. A process for augmenting or enhancing the hazelnut flavor of a hazelnut flavored foodstuff comprising the step of adding to a hazelnut flavored foodstuff from about 0.0005 ppm up to about 250 ppm of a composition of matter consisting essentially of 2,5-dimethyl-3-acetylfuran and 3,5-di-(2-methylpropyl)-1,2,4-trithiolane, the ratio of said 2,5-dimethyl-3-acetylfuran: 3,5-di-(2-methylpropyl)-1,2,4-trithiolane being from 1:1 to 1:0.1.

* * * * *